United States Patent [19]
Coakley et al.

[11] Patent Number: 5,236,673
[45] Date of Patent: Aug. 17, 1993

[54] OZONATION SYSTEM FOR TREATMENT OF WATER IN COOLING TOWERS

[75] Inventors: Timothy G. Coakley, Rock Hill; Alfred J. Horton, Jr., Howells; Bruce E. Kaplan, Woodridge, all of N.Y.

[73] Assignee: Reztek International, Inc., Mountaindale, N.Y.

[21] Appl. No.: 685,544

[22] Filed: Apr. 15, 1991

[51] Int. Cl.$^5$ .............................. B01J 19/08
[52] U.S. Cl. .................... 422/186.07; 422/186.18; 422/3; 422/28
[58] Field of Search ............... 422/186.07, 186.18, 422/3, 28

[56] References Cited

U.S. PATENT DOCUMENTS

| | | | |
|---|---|---|---|
| 3,616,355 | 10/1971 | Themy et al. | 204/149 |
| 4,172,786 | 10/1979 | Humphrey et al. | 210/57 |
| 4,417,966 | 11/1983 | Krauss et al. | 204/176 |
| 4,640,782 | 2/1987 | Burleson | 210/748 |
| 4,774,062 | 9/1988 | Heinemann | 422/186.19 |
| 4,869,881 | 9/1989 | Collins | 422/186.18 |
| 4,872,959 | 10/1989 | Herbst et al. | 204/109 |
| 5,106,497 | 4/1992 | Finnegan | 210/192 |
| 5,114,576 | 5/1992 | Ditzler | 210/195.1 |

Primary Examiner—Donald P. Walsh
Assistant Examiner—Daniel J. Jenkins
Attorney, Agent, or Firm—Schweitzer, Cornman & Gross

[57] ABSTRACT

An improved system for treatment of cooling tower water using ozone as a biocide. A self-contained unit is supplied with compressed air which is introduced to ozone generating electrodes at a constant flowrate. The ozone is mixed with tower water and then returned to the cooling tower. A sampling probe allows for constant monitoring of the ozone content of water coming from the tower. The volume of ozone mixing with the tower water is accordingly constantly adjusted. The system also includes safety control features to monitor system operation and provide shutoff in the event of malfunction.

14 Claims, 7 Drawing Sheets

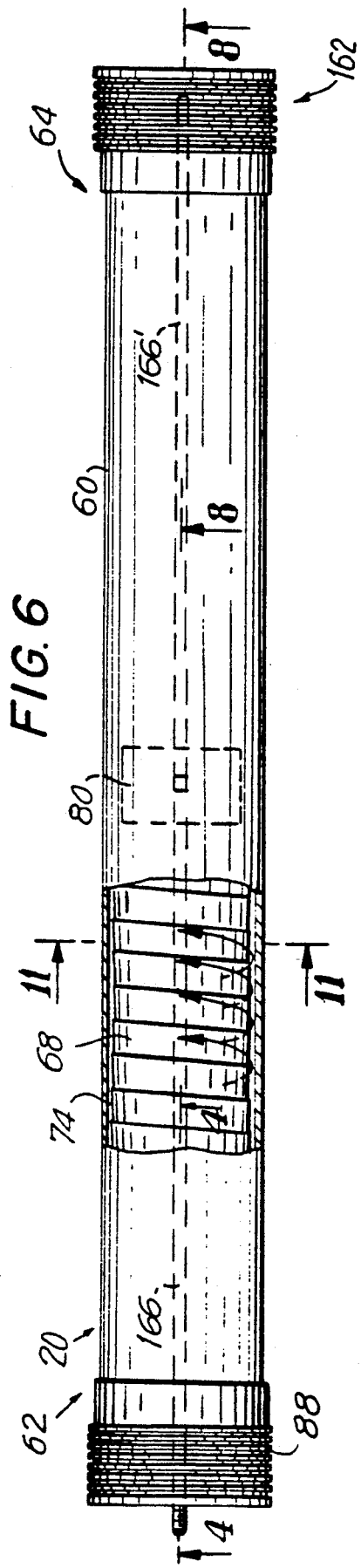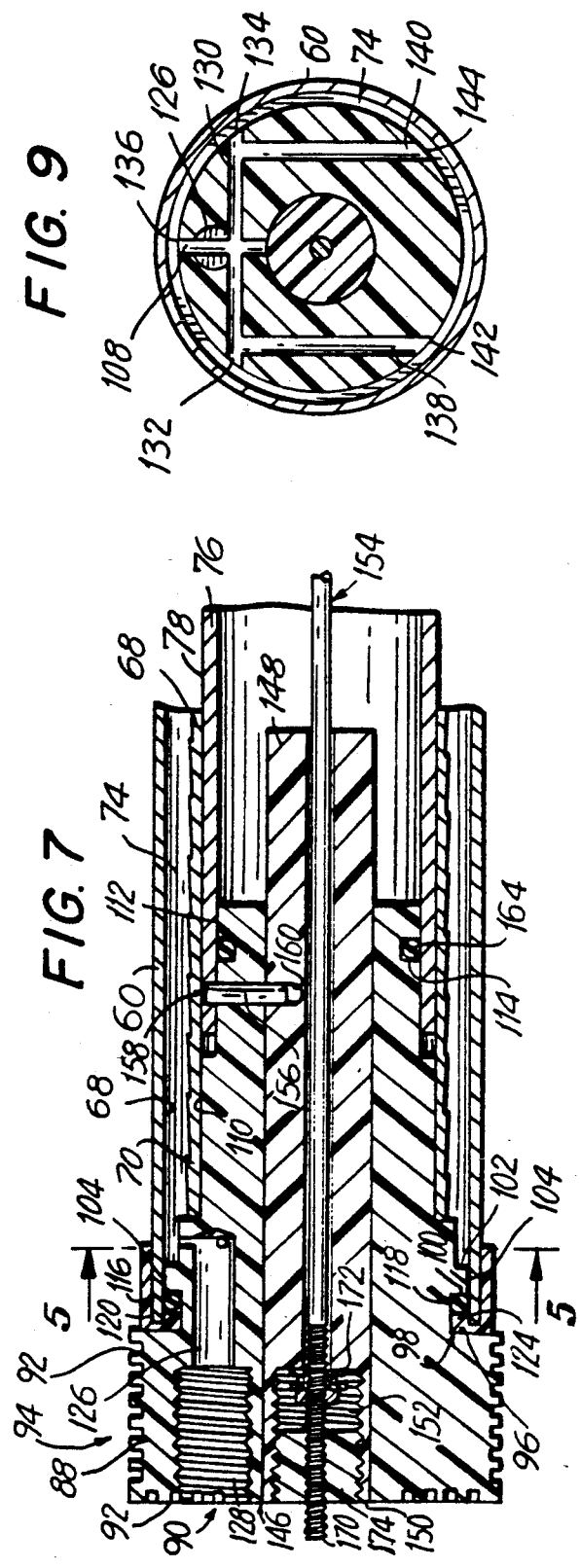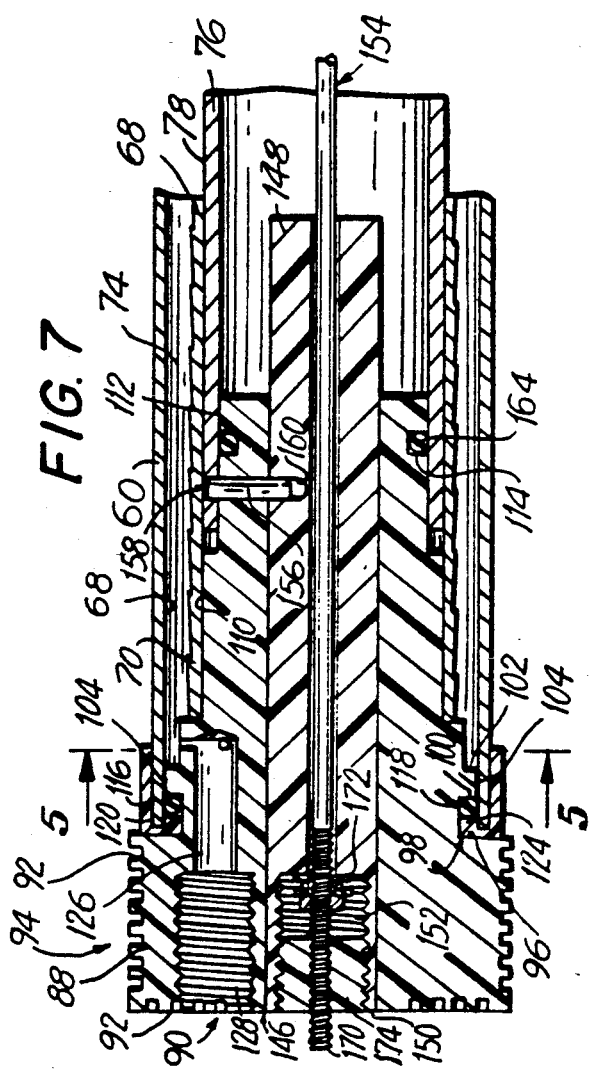

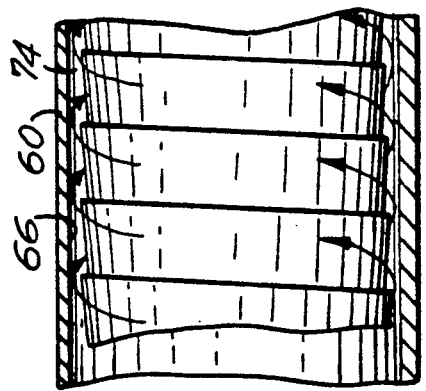
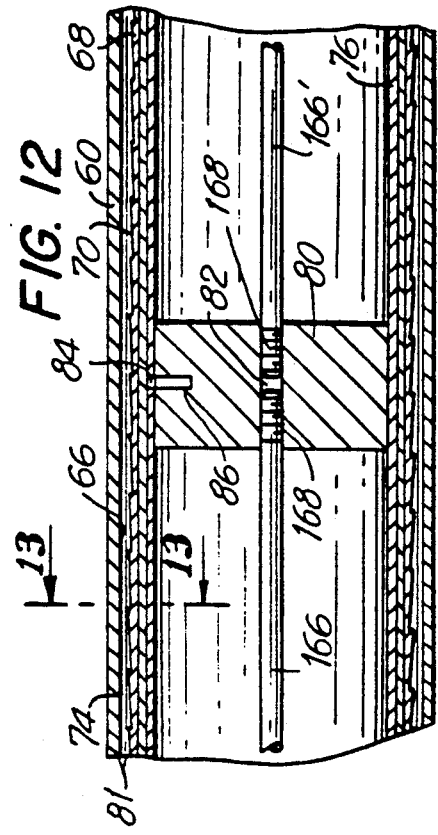
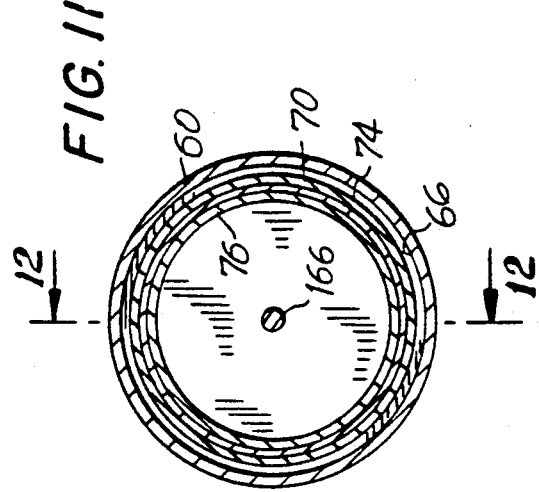
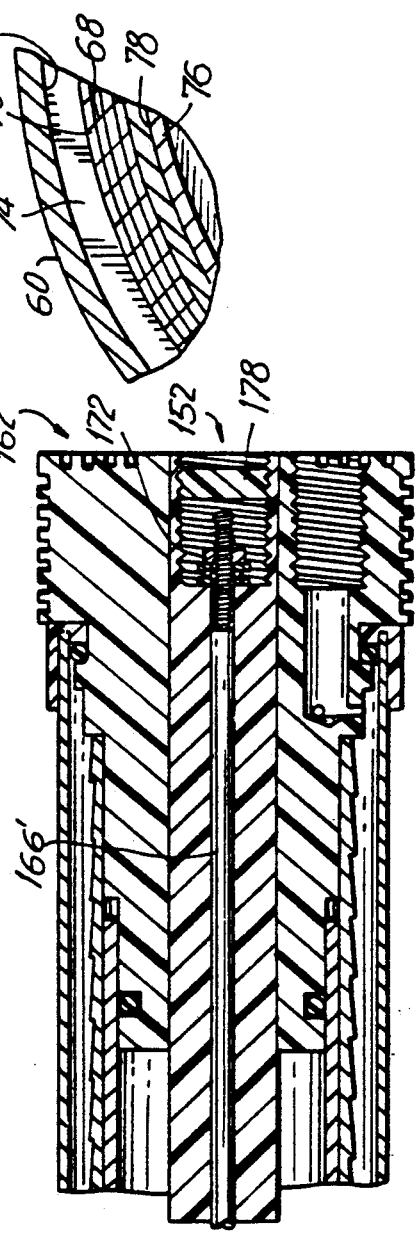

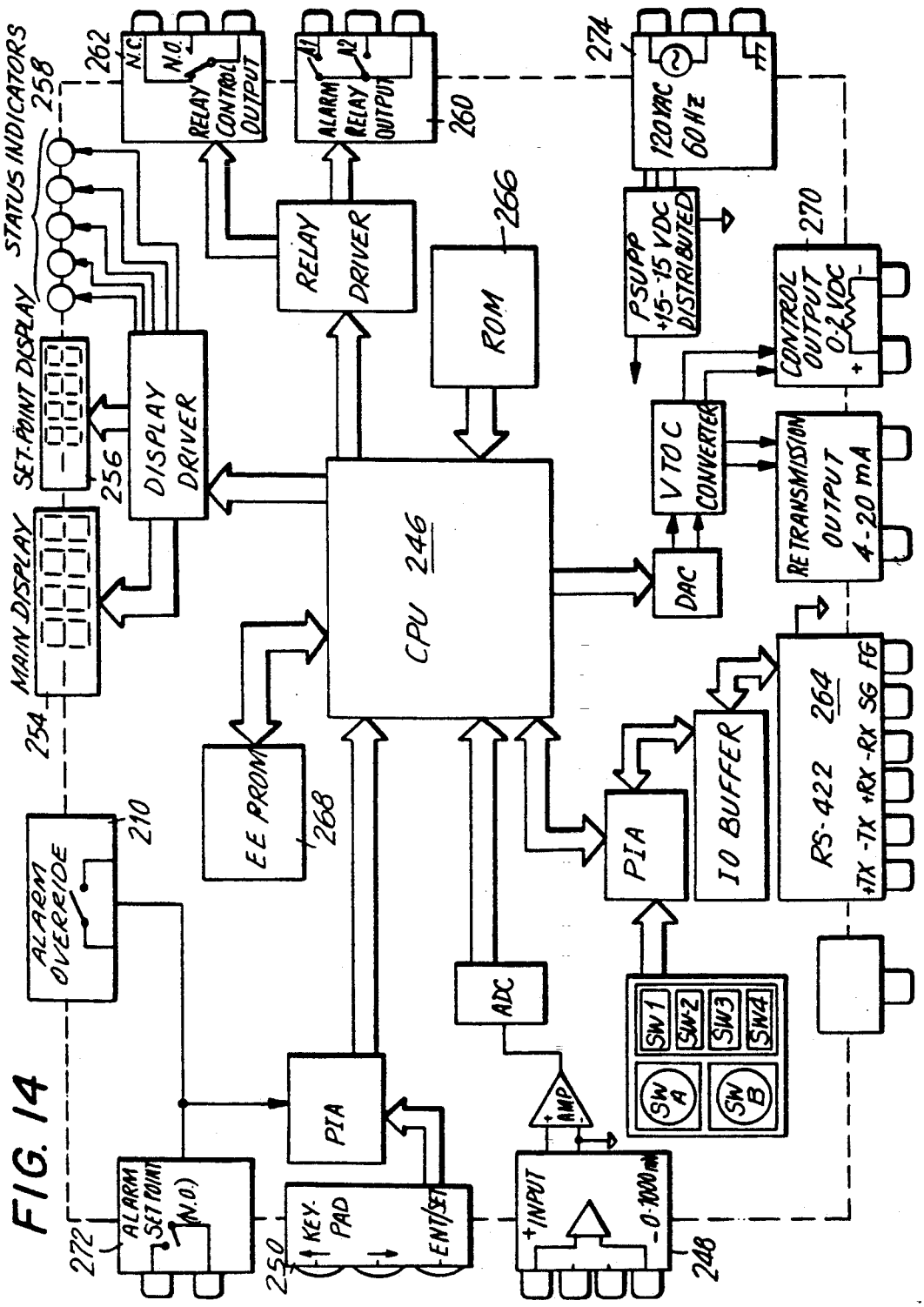

OZONATION SYSTEM FOR TREATMENT OF WATER IN COOLING TOWERS

BACKGROUND OF THE INVENTION

1. Introduction

This invention relates to an improved ozonation system for treatment of cooling tower water typically utilized in conjunction with the operation of large-scale cooling and air-conditioning equipment and, more particularly, pertains to significant advances in the efficient operation of an ozone generation system keeping it at optimal operation condition, protecting the ozonation system, and informing others of problems within the system.

2. Prior Art

Ozone has been used in the treatment of drinking water for more than 100 years. While there is much literature on the subject, the more modern work done with ozone is summarized in an article by Maurice Ogden of Water Treatment Corp. appearing in the June, 1970 issue of "Industrial Water Engineering". This article discusses the use of ozone to treat water. It mentions an ozone treatment plant built and put into operation in 1949 by the Philadelphia Water Works, and reviews advances in acid-resistant materials for air conditioning systems and breakthroughs in electrical circuitry design allowing for the development of a more efficient ozone generating unit.

U.S. Pat. No. 4,172,789, issued Oct. 30, 1979, discloses the type of structure described in the above article, namely a water tower with means to generate ozone, mix the water tower water with the generated ozone, and then return the ozone enriched water to the tower.

H. Banks Edwards discusses the use of ozone as "an alternate method of treating cooling tower water" in the Journal of the Cooling Tower Institute, Vol. 8, No. 2, 1987, page 10. Edwards illustrates a more sophisticated cooling tower than that of the '786 patent. The article discloses dividing the water coming from the tower so a sample portion goes back into the tower while the remaining portion is ozone enriched.

A paper was presented on "Ozone Treatment of Cooling Water: Results of a Full-Scale Performance Evaluation" at the 1989 Cooling Tower Institute Annual Meeting by G. Darell Coppenger, Benjamin R. Crocker, and David E. Wheeler. The paper also verified the many benefits of oxygenation. It shows (FIG. 3, page 21) the use of a personal computer to operate the system and means to monitor the quality of the water and the voltage potential across an ozone sensing probe.

Further developments are illustrated in the catalog of Ozonair International Corp. of South San Francisco, Calif., which illustrates specially designed sensor electrodes with solid state and transistorized circuitry. Another sophisticated example is the ozone self-contained injection system of Prosys of Chelmsford, Mass.

All of these systems, while feasible and performing in the field, do not develop a sufficient volume of ozone for the number of electrodes. They do not provide true commercial benefits.

OBJECTS AND ADVANTAGES OF THE PRESENT INVENTION

A principal object of the present invention is to provide a new and improved ozonation system to treat cooling tower water.

Another object of the present invention is to provide a self-contained ozonation unit with an advanced electrode design capable of providing substantially increased levels of ozone at a reduced cost.

Yet another object of the present invention is to provide an ozonation unit with the ability to monitor the ozone levels in water leaving the cooling tower and adjust the amount of ozone entering the system on a continuous basis.

Still another object of the present invention is to provide a unit of the character described having a control system which constantly test various parameters of the system, to provide appropriate signals upon development of operational problems.

Still a further object of the present invention is to make an ozone treatment system which is practical in operation.

Still another object of the present invention is to provide a unique design of electrode which is comparable in dimensions to current electrodes but results in vastly improved ozone generating efficiency.

Still yet a further object of the present invention is to provide a unit of the character described which is inexpensive and simple to manufacture and yet durable in use.

BRIEF DESCRIPTION OF THE PRESENT INVENTION

The present invention consists of a self-contained microprocessor-controlled ozonation unit incorporating a unique ozone-generation electrode. A first air inlet supplies compressed air at approximately 100 psi which is filtered and dried, resulting in a highly depressed dewpoint. The filtered and dried air is dropped in pressure from 100 psi to approximately 3 psi, the dewpoint correspondingly dropping to about $-140°$ to $-160°$ F. The air then passes through a flowmeter which controls the volume of air directed to ozone-generating electrodes of the unit. The electrodes excite the oxygen in the air from its stable form ($O_2$) to its unstable ($O_3$) ozone form.

The unique electrode consists of a central electrical connecting rod which is supported by insulating inserts at its proximal end points within a cylindrical metallic outer tube. An inner concentric conductor tube is electrically connected to the central connector rod. A tubular silicon dielectric material is placed between the inner and outer tubes and is spaced from the outer tube. The inner surface of the outer tube and the outer surface of the silicone dielectric form an air gap across which a high voltage potential is placed, causing corona discharge which converts the oxygen in the air gap to the ozone form.

Air is introduced into the electrode air gap by means of a series of holes which, in conjunction with the construction of the dielectric, cause a spiral air flow through the electrode. Because of this spiral flow, the air remains within the electrode for a greater length of time than with a direct flow, allowing for a greater degree of ozone production. The air exits the electrode through a similar arrangement of holes at the second end. The ozone enriched air that emerges from the electrode carries approximately 500 percent more ozone than similarly dimensioned prior art structures.

The computer-based control system includes an oxidation-reduction potential (ORP) probe which monitors the ORP level of the tower water. A controller adjusts the voltage applied to the electrodes on a continuous basis to provide a varying ozone production. The ozone production level is proportional to the oxidation-reduction potential sensed by the ORP probe, such that the ORP of the water, which is indicative of the level of all oxidants present in the water including ozone, ozonides, secondary biocides, chlorine present in the make-up water, aldehydes and the like, is maintained at a proper level. The system also monitors the protective devices of the unit, issuing appropriate alarm signals when an out-of-range condition is experienced. The alarm signals may be broadcast both locally and remote to the system.

When the ORP is in the proper range, as maintained by the present system, organic material present as water contaminants in the system, which can cause the attachment of scale to the fluid contacting surfaces (tower, lines, etc.) of the air conditioning/cooling system to which the water supply is connected, are effectively and continuously oxidized and rendered incapable of fouling the system. The water system thus can operate for longer periods without maintenance and without the necessity of flushing and disposal of accumulated sludge.

In distinction to the prior art, the present invention provides an ozone level of 0.03 to 0.07 ppm, which allows secondary biocides, such as aldehyde soaps formed from the reaction between ozone and contaminants in the water, to remain active. This maintains a positive residual for several days in the event of system shutdown. By maintaining an ORP in the range of 550-650, offgassing of ozone from the water which occurs at elevated ORP levels is avoided, thus providing improved environmental benefits and eliminating the risk of corrosion due to the effects of ozone gas.

The water subject to treatment is drawn from the cooling system's water tower by a pump and is divided, a portion of which being directed to a venturi which draws the ozone-enriched air exiting from the electrodes into a venturi and blends the air and water portion together. The air-water blend is combined with the remaining portion of the drawn water by a motionless mixer, and is returned to the water tower. The ORP probe constantly monitors the untreated water portion to ascertain the ORP and thus the level of total oxidants present, the system constantly adjusting the electrode voltage, either reducing, increasing, or stopping ozone production as required to maintain the monitored water at the correct ozone level.

DESCRIPTION OF THE DRAWINGS

FIG. 6 is a side elevational view of an electrode, partly in section and partly cut away;

FIG. 7 is an enlarged cross sectional view of the left end of the electrode taken along the line 7—7 of FIG. 6;

FIG. 8 is an enlarged cross sectional view of the right end of the electrode taken along the line 8—8 of FIG. 6;

FIG. 9 is an enlarged cross sectional view of the arrangement of the holes at the left end of the electrode taken along the line 9—9 of FIG. 7;

FIG. 10 is a schematic showing air travel through the electrode;

FIG. 11 is a cross sectional view taken along the line 11—11 of FIG. 6;

FIG. 12 is an enlarged cross-section view of the central portion of the electrode detailing the connection between the central rod and inner tube;

FIG. 13 is a further enlarged cross-sectional view showing the structure of the electrode air gap; and FIG. 14 is a block diagram of the controller of the invention.

DETAILED DESCRIPTION OF THE INVENTION

Figure 2:
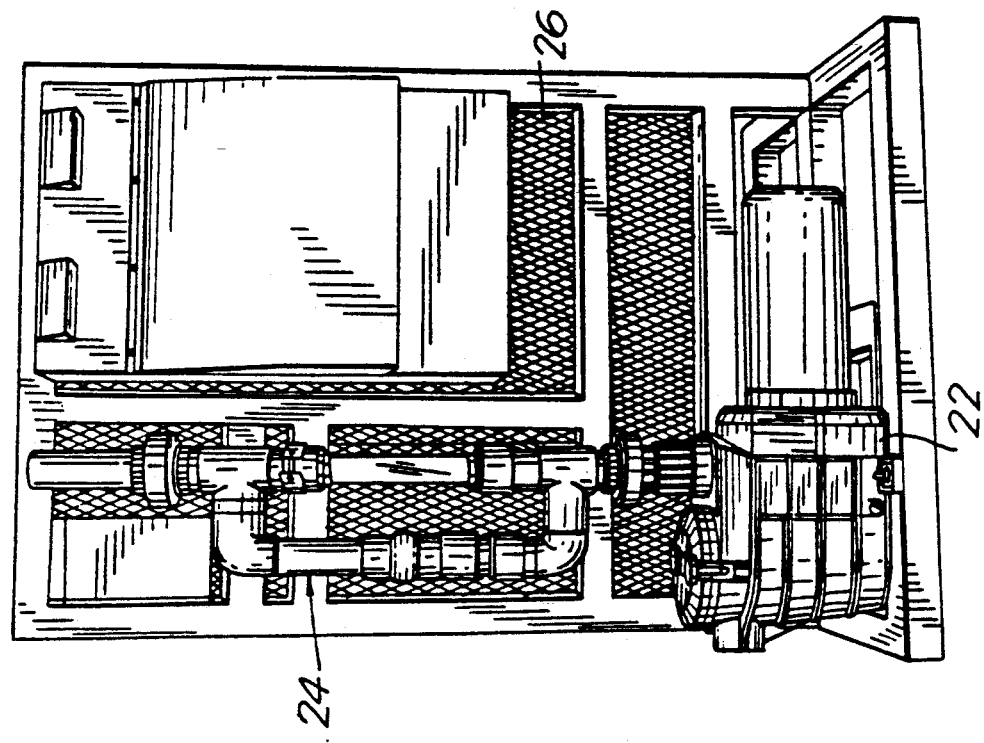
FIG. 2 is rear elevational view of the same unit.
Figure 1:
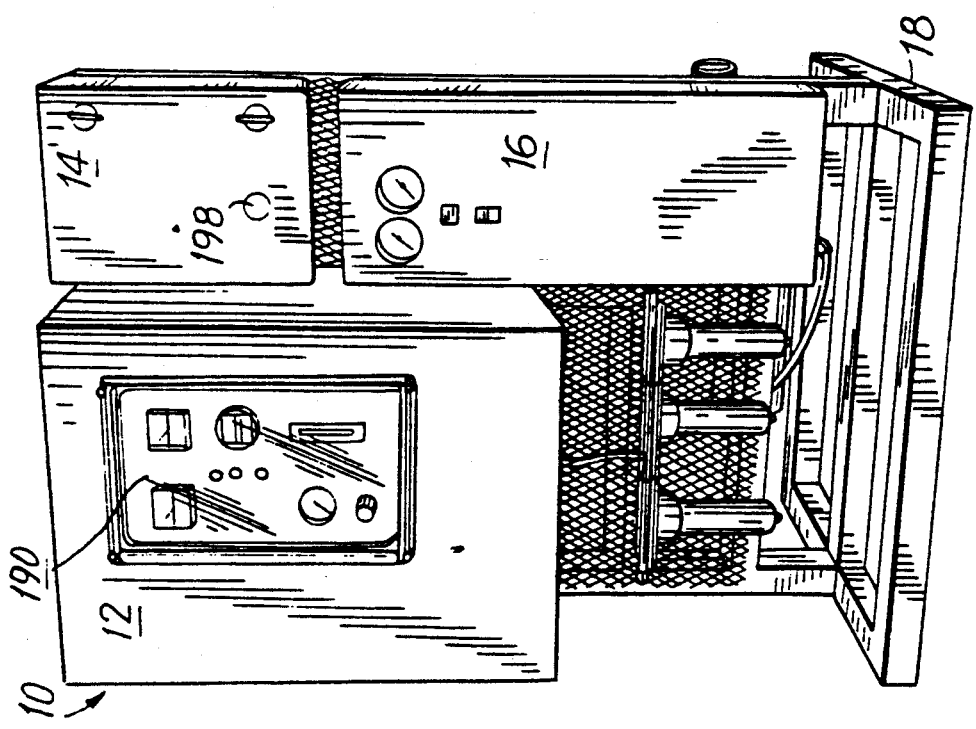
FIG. 1 is a front elevational view of a unit comprising our invention.

Turning in detail to the drawings and initially to FIGS. 1 and 2, there is shown an ozonation treatment unit 10 containing our new improved ozone generator. The cabinets 12, 14 and 16 house the electrical components required for system operation. The cabinets and associated mechanical gear are mounted on a stand and pedestal frame 18. The electrodes (not shown) which produce the ozone are mounted horizontally, while the water to be treated is pumped by pump 22 and is treated within the piping generally indicated a 24. Protective gratings 26 are utilized as required to further isolate portions of the apparatus.

Figure 3:
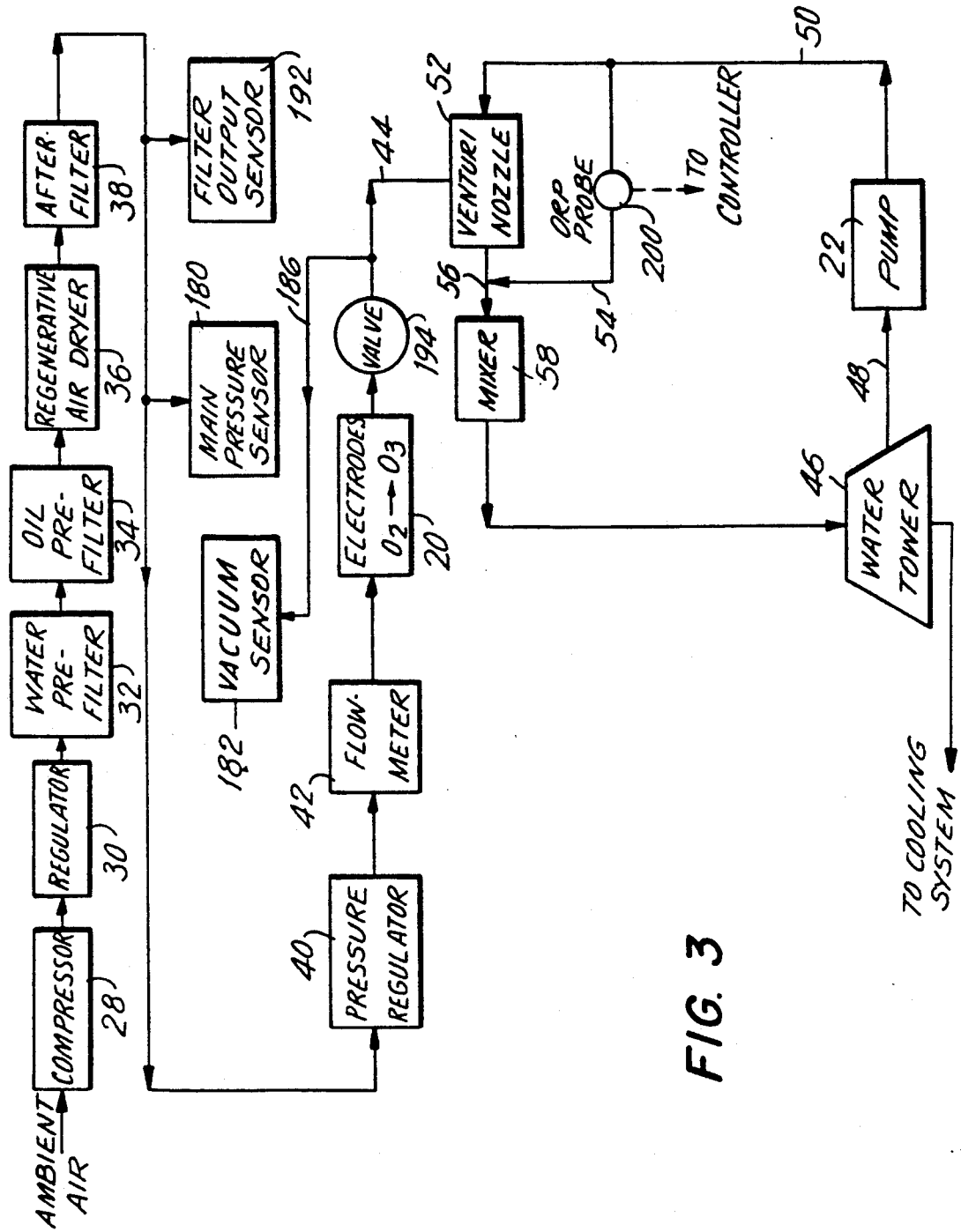
FIG. 3 is a schematic showing the principal mechanical elements within the unit.

As shown in the flow diagram of FIG. 3, atmospheric air is compressed by compressor 28 up to approximately 100 psig at a 5 scfm flow rate. The compressed air is then delivered to a pressure regulator 30 and then to water pre-filter 32 to remove the bulk of the moisture from the compressed air. The treated air is then passed through oil removal pre-filter 34. Both the pressure regulator and the filters are available from SMC Lakewood, N.J. The double-treated air, still at approximately 100 psi, is then passed to a heatless regenerative air dryer 36. The dryer contains a desiccant which purges itself approximately every four minutes, such as the Model No. DWH-5, manufactured by Hankison of Pittsburgh, Pa. At this point the air is still at 100 psi, but it has a $-100°$ F. dewpoint.

The dried air is then passed through after-filter 38 which removes any dust and particulate matter that the air may have picked up from the desiccant in the air dryer 36. The after filter may be the SMC Model No. NAFD3000-NO. 3. Pressure regulator 40 then drops the pressure from 100 psi to approximately 3 psi. The dewpoint also drops to between $-140°$ to $-150°$ F. An acceptable regulator is also available from SMC as Model No. R05-02-000.

Flowmeter 42 controls the volume of air directed to the electrodes 20. The number of electrodes may be varied depending on the volume of air to be treated. The flow rate through the electrodes is constant, irrespective of the level of ozone produced. A typical flowmeter is made by Dwyer of Michigan City, Ind., Model No. RMA-9-SSV. There may be four, eight or twelve electrode assemblies 20, depending upon how much ozone has to be produced to properly treat the volume of water in the water tower. The ozone-enriched air exits the electrodes via a conduit 44 as will be explained.

A water pump 22 draws water from the water tower 46 via a conduit 48. The water exits pump 22 via conduit 50 to a venturi nozzle 52 where the water is accelerated, the resulting pressure drop drawing the ozone-enriched air in from the conduit 44. A typical venturi is manufactured by Mazzi of Bakersfield, Calif., under Model No. 1584A (Kynar). A portion of the water from the tower 46 bypasses the venturi via conduit 54 and rejoins the ozone-enriched water at connection 56. The combined stream passes into a motionless mixer 58 to ensure complete dispersal of the ozone throughout the water. An acceptable mixer is manufactured by Koflo of East Dunder, Ill., Model No. 1¼-80-4-3U.-1. Treated water is then returned to the water tower 46.

One of the principal features of invention is the novel structure for the ozone generator electrode assemblies 20. As can be seen in FIGS. 6–13, the ozone generator consists of a plurality of electrodes 20 each having an outer tube 60 with a left proximal end 62 detailed in FIG. 7 and a right distal end 64 detailed in FIG. 8. Positioned within and spaced from the inner surface 66 of the outer tube is a silicone tube 68 (FIGS. 6 & 7) defined by an outer surface which is formed of wrapped fiberglass and silicone stripping 70 (FIG. 13) defining a spiral configured leading edge or step 72 advancing diagonally to the upper right through the electrode as seen in FIG. 6. This spiral edge causes the air to travel in a swirling pattern as it travels through the electrode, as depicted in FIG. 10, thus increasing residence time in the electrode. A Flex tab 7701-150 silicone Turbo Tube is preferred for use as the tube 68.

The outer tube 60 and silicone tube 68 are so dimensioned as to leave a gap 74 between the outer tube inner surface 66 and the silicon tube spiral wrap outer surface 70, as best seen in FIGS. 11 and 13. The gap varies somewhat because of the spiral wrapping, but it averages slightly less than 1/16 of an inch. It has been found this provides a maximum efficiency for the production of ozone, although it may not be the only commercially acceptable width.

Positioned within tubes 60, 68 and having an axis concentric with both tubes is a center, inner tube 76 (FIG. 7), having an outer surface 78. A solid metallic center plug 80 (FIG. 12) is positioned within the center tube 76 and includes a coaxial centered, threaded bore 82. The plug is positioned at approximately the middle of the center tube, equidistant from each end. Once it is so located, a hole 84 through the wall of the center tube 76 and a radial bore 86 in the insert are aligned. A pin (not shown) is then placed within the hole and bore to fixedly position the two elements.

A left end cap 88 (FIG. 7) is specifically designed for the proximal end of the electrode. The cap, formed of PVC or other insulating composition, has an outer end wall 90 having a plurality of corona-minimizing circular grooves 92 and an outer side wall portion 94 of cylindrical configuration and of somewhat greater diameter than the outer diameter of the outer tube 60. The wall portion 94 also includes a plurality of the grooves 92. The rightmost end of the outer side wall portion 94 terminates in a shoulder 96 which defines one side of a deep radial groove 98. The groove 98 supports a sealing system for the electrode 20. The groove 98 is defined by shoulder 96 and, at its other end by wall 100 which, with opposed shoulder 102, defines a circular step portion 104 whose outer diameter approximates the inner diameter of the outer tube 60. A third step portion 106 is of lesser diameter than the inner diameter of the outer tube 60. This step portion bears a series of radial bores, such as bore 108 seen in FIG. 7, which pass the pressurized air into the space between the outer tube 60 and silicone tube 68, as will be discussed. The end cap 88 terminates at its interior end with fourth and fifth step portions 110, 112, each of lesser diameter than its predecessors. Fourth step 110 is of a diameter chosen to contact and support the inner surface of the silicone tube 68, while fifth step 112 similarly supports the inner surface of the end of center tube 76. An O-ring 164 in radial groove 114 in the step 112 seals the center tube to the cap.

The outer and center tubes 60 and 76 are preferably of nickel-plated aluminum. The outer tube may have an outer diameter of 2 inches with a 0.065 inch wall thickness, while the inner tube is of 0.058 inch wall thickness and a 1.5 inch outer diameter. The silicone tube is of nominal 0.095 wall thickness, with a 1.5 inch inner diameter. The length of the outer tube is 17.125 inches, the outer tubes being sized proportionally.

A sealing system located within the groove 98 includes a generally L-shaped silicone gasket 116, one leg 124 of which occupies a part of the groove. The remainder of the groove is filled by an O-ring 118. The gasket 116 has a notch 120 located at the intersection of the legs 122, 124 of the "L", whose width is chosen to firmly grip the end of the outer tube 60. The O-ring 118 and the gasket 116 form a sufficiently tight seal to prevent leakage of any ozone enriched air from the electrode.

In order to permit the passage of air into the space defined between the outer tube 60 and the silicone tube 68, a longitudinal bore 126 in the cap 88 passes in from its outer end wall 90. The bore has a threaded portion 128 to accept a mating connector.

As seen in FIG. 9, the bore 126 connects with a series of transverse bores in the end cap, each of which terminate at the stepped portion 106. Bore 126 intersects with chordal throughbore 130 having opposed ends 132, 134 and perpendicular radial bore 108 bearing end 136 as seen in FIG. 7. The chordal bore 130 also joins with the ends of a pair of parallel chordal bores 138, 140 perpendicular thereto, whose distal ends form yet another pair of exits 142, 144. Accordingly, the bores 108, 130, 138, and 140 provide a series of passageways connected to bore 126 and which all terminate in the stepped portion 106 to provide an entranceway path for the air entering the electrode. While a single hole or any arrangement of holes will introduce the air into the intra-tube air gap 74, we have found that arrangement as disclosed herein appear to present an optimal introduction of air to the gap. In particular, such introduction occurs with the diameter of exits 132, 134 and 136 being 0.0625 and diameter with exits 142, 144 being 0.1875 inch diameter.

The end cap 88 further includes a main throughbore 146 in which a cylindrical, rod-supporting insert 148 (FIG. 7), preferably made of teflon, is placed. Passing inwardly from the distal end wall 150 of the insert is a blind bore 152 which communicates with concentric throughbore 154. The end wall 150 of the insert is aligned with the end wall 90 of the end cap 88 to present a smooth, substantially common end surface. This alignment may be maintained by a pin 156 passing through aligned radial throughbore 158 in the cap 88 and blind bore 160 in the insert 148. An appropriate notch (not seen may be placed in the end of the center tube 76 to provide clearance for the pin.

Positioned at the right end of the outer tube 60 is a right end cap 162 and associated elements. It is identical to the left end cap except that it is rotated about the longitudinal axis of the electrode so that it is in a position 180° opposite the position of the left end cap. Thus, the exit ports 130, 132, 136, 142 are in opposite and inverted orientation to those in the left end cap. The ozone-enriched air passes out of the electrode exits through these opposite locations. Ozone is generated by the creation of a high-voltage electrical field between the center and outer tubes 60 and 76.

Current is introduced into the electrode by a pair of central electrical connecting rods 166, 166' which extend between the two end caps and which are joined together at the plug 80, best seen in FIG. 12. Each of the rods are provided with first threaded end portions 168 which mate with the threaded bore 82 in the plug. The rod 166 extends through the teflon insert 148 of left cap 88, as seen in FIG. 7, to provide an electrical connection terminal. Its distal end includes a threaded portion 170 which passes out through the blind hole 152 and beyond the end wall 150. The rod 166 is maintained in proper position by washer and nut assembly 172. A threaded end seal 174, preferably of teflon and having a central bore for the rod is then placed within the blind hole, leaving the end of the rod exposed for electrical contact. The right side rod 166' is somewhat shorter than the left rod, such that it terminates within the blind hole 152 in the right side cap, as shown in FIG. 8. Its threaded end 176 is similarly affixed with a washer and nut assembly 172, the blind hole at this end being capped by solid threaded teflon cap 178. The outer tube 68 serves as the opposed electrical connection for the electrode, it being mounted in a conventional manner in an electrical connector which also serves as the holder for the electrode.

Figure 4:
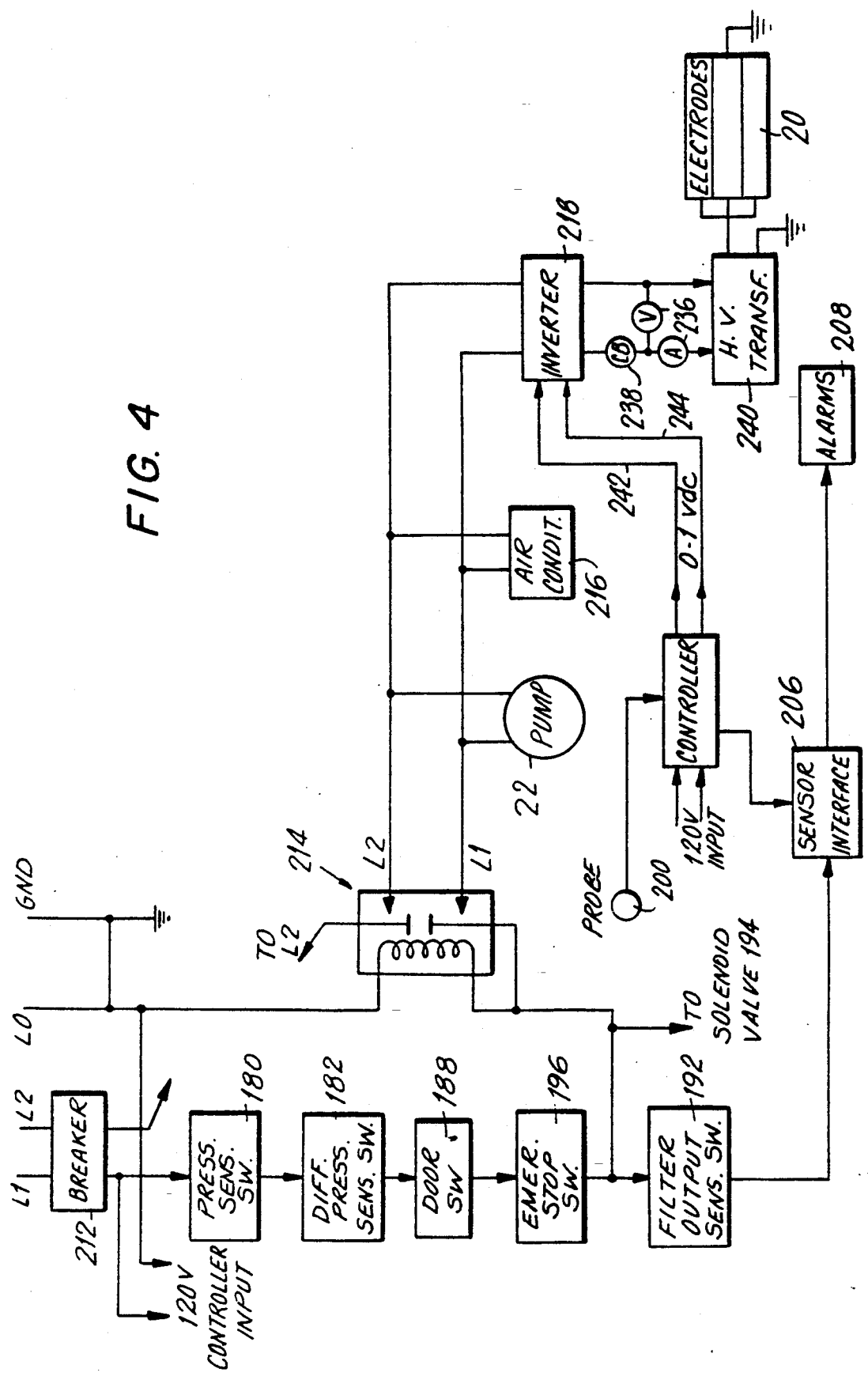
FIG. 4 is a schematic of the electrical elements within the unit.

Another feature of the present invention is a series of safety devices which protect the system and allow the system to operate in a remote location, preferably proximate the water tower. Among the features that allow this to occur are a plurality of safety control systems. . Turning to FIGS. 3 and 4, the first feature is an air pressure safety switch 180. As air is the raw material for ozone production, an insufficient airflow lessens or halts ozone production and can result in unnecessary wear and perhaps damage to the electrode dielectric. Furthermore, the air dryer 36 will not work properly if there is an insufficient supply of compressed air coming into the system. Accordingly, air pressure safety switch sensor 180 is located on the air supply conduit just before the compressed air enters the pressure regulator unit 40. If the air pressure sensor reads an air pressure of less than 30 psi, the system will automatically shut down, and will not restart until the air pressure sensor reads a pressure of 30 or more psi. In addition to the system shutting down, an alarm is energized by means of a light or an audible sound in order to alert an operator that there is a problem within the system.

The second safety feature is vacuum switch 182. A sensing line 186 connects to the output conduit 44 from the electrodes 20. If the switch does not read a vacuum of approximately 20 inches of mercury, it is an indication that the venturi 52 has shut down. If this occurs, the switch automatically turns off the system. The lack of the proper vacuum suggests that the pump inlet filter is clogged, the lines to the tower are blocked, or the pump 22 has shut down for some reason. The switch will therefore shut the whole system down until such time as the alarm condition has been cleared. In the case of a drained-down tower, the system will sense the absence of water and thus automatically protect the ozone generator and treatment system.

The next safety feature is the door switch 188 (FIG. 4). The panel 12 provides access to the electrodes 20 as seen in FIG. 1. If this door is open, switch 188 opens. As there is high voltage present in the generator cabinet, the door switch minimizes the risk exposure of a person to such voltages.

Positioned upstream of the air pressure sensor 180 is pressure sensor 192 FIG. 3) which monitors the operation of filters 32, 34, and 38. A filter discharge pressure drop on the outport line from after-filter 38 to a predetermined level, such as 80 psi, indicates that one or more of the filters may be plugged or otherwise not be functioning properly. Therefore, this pressure sensor is set to trigger an alarm before alarm 180 operates. When this alarm sounds, the filters can be checked to make certain they are working properly. This may require routine maintenance of filter elements. With a further reduction in pressure, sensed by alarm 180, the system will shut down.

The next safety feature is the solenoid valve 194 in electrode output line 44. If the system shuts down for any reason, the solenoid valve will automatically close the conduit. This prevents water which might back up from the venturi system into line 44 from reaching the electrodes. The valve will remain in its closed state until such time as the alarm condition has been removed.

The next safety feature is an emergency stop switch 196 (FIG. 4) which includes a large actuator 198 on the front panel of cabinet 14 of the unit 10 as seen in FIG. 1. Depressing the switch removes electrical power from the entire system. In addition, an electrical disconnect mounted at the rear of the main cabinet removes all power to permit safe inspection and maintenance of the unit.

The final safety system operates in conjunction with the oxidation reduction potential probe 200, whose operation will be discussed infra in connection with ORP controller 202, shown in FIG. 14. When the user first initiates operation of the system the oxygen-reduction potential of the water is typically at an unsatisfactory level, which would normally cause the system to enter an alarm state as issued by controller 202 passing a signal to sensor interface 206. A bypass override switch 210 allows the alarm to be overridden during this initial period. The controller will allow the generation of ozone at the maximum level until the oxidation-reduction potential in the tower water reaches an acceptable level. Once the system is operating within the desired parameters, the bypass switch is turned to the normal position. The alarm system is then operative.

After the initial phase, when the sampling probe 200 senses a drop in ORP in the water coming from the water tower to a point below the alarm set point, the alarm system will be triggered, subject to a programmed 1.5 hour delay. Sometimes a significant amount of an organic contaminant will be introduced in the water, such as leaves being blown into an open-top water-tower during a windstorm. Under these conditions the system has to be given time to increase its ozone production to compensate for the additional impurities. If, after an hour and a half the ORP has not reached the proper level, the alarm system will set off a visual and/or audible alarm at 208. The system will continue to operate, however.. If the alarm is not answered in an additional two hours then the system will shut down although the alarm will continue to remain active.

A watchdog portion of controller 202 compares consecutive ORP readings. In the event of a fouled or dirty probe, the ORP readings will remain constant for an extended interval, such as 1 hour. In such a case, an alarm signal is sent to a chosen remote location on an RS 422 or 232 interface, while ozone output is automatically reduced to zero. Similarly, if the ORP probe fails, the controller will send an appropriate signal, while halting ozone production as required.

Description of Electrical Circuitry

Electrical power comes into this system through Lines $L_1$, $L_2$ which provide 240-volt, single-phase power, each 120 volts to ground or neutral $L_o$. In order to protect the system against power surges, a circuit breaker 212 is positioned at the entrance to the electrical system. One hot leg, such as $L_1$, carries each of the switch/sensors, in series, such that each sensor can control the system.

Power is supplied through line $L_1$ to main contactor relay 214, which controls the application of full 240 volts to the pump 22, system cooling equipment 216, and to invertor 218 which powers the bank of electrodes 20. The differential pressure switch 192 activated by the three filters 32, 34, 38 is not in series with the contactor, as its activation does not result in a system shutdown. Upon a pressure drop of the predetermined amount the switch 192 is activated, sending an alarm signal to sensor interface circuit 206. This results an audible or visual alarm at 208. If the failure escalates pressure sensing switch 180 becomes energized, causing system shutdown.

Figure 5:
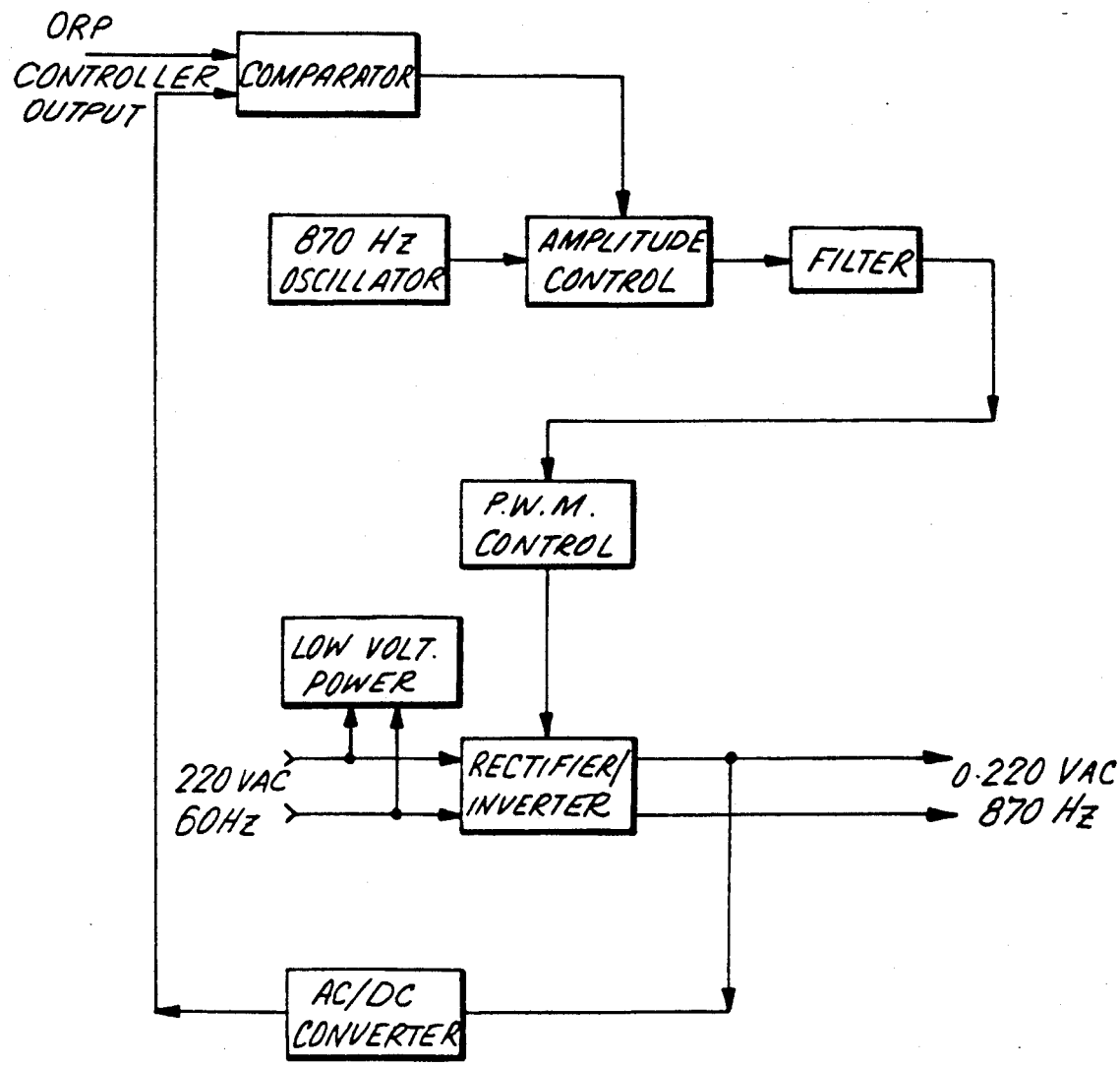
FIG. 5 is a block diagram of an inverter used in the invention.

Invertor 218 provides the high voltage AC required for operation of the electrodes. As shown in FIG. 5, the invertor utilizes a 0-1 volt dc output from controller to provide a nominal 0-220 volt output. The input is directed to a comparator 220, which compares the input to a reference voltage generated by converter 222 which senses the output of the invertor. Comparator 220 generates an error signal output which is used to vary the amplitude of a 870 hz signal produced by oscillator 224. After appropriate filtering at 226, the control signal is applied to pulse width modulator 228, which modulates a rectified 220 volt input in bridge circuit 230. The output on lines 232, 234 is a variable 0-220 volt ac signal at 870 hz. It has been found that optimal oxygen-ozone conversion occurs at this frequency of applied voltage.

The output of invertor 218 on lines 232, 234 may be monitored by ammeter-voltmeter pair 236 and protected by circuit breaker 338. The voltage drives high voltage transformer 240, having a nominal 10,000 volt output at 220 volt input, its high voltage output being used to energize the electrodes 20.

The control voltage for the invertor 218 is generated by ORP controller 202, whose input is generated by oxygen-reduction potential sensing probe 200, which is of known construction, as exemplified by the Sensorex model S220CD. The output of the probe varies in a range of approximately 0-1000 mV, depending primarily on the ozone concentration of the sample, although other constituents, primarily chlorine, may affect its value. Chlorine, however, is short-lived, and in a recycling system where the water is not substantially replenished, the ORP reading is a significant indicator of ozone concentration. The probe output is utilized by the controller to place the control voltage on lines 242, 244 which corresponds to an invertor output of between approximately 90 and 180 volts, inversely proportional to the probe output. In general, an output voltage of approximately 125-150 volts across the transformer 240 primary is required to generate ozone, depending on the specific flowrate and construction variables. Thus, an invertor output of 90 volts corresponds to a virtual zero ozone output.

The controller 202 of the present invention, depicted in FIG. 14, is a microprocessor-driven unit which interfaces the ORP probe and invertor and provides the control mechanism for operation of the ozone-producing electrodes. In particular, the microprocessor CPU 246 is provided with an appropriate interface 248 with the ORP probe, whose output is typically a 0-1000 mv dc signal. A keypad 250 for programming and entering data, is also provided. The CPU 246 also controls main digital display 254, which displays the ORP value sensed by the probe 200, a set point display 256, which indicates the targeted ORP and status indicators 258 which set forth the condition of the controller. An alarm relay output 260 provides ORP-derived alarm signals to the audio and/or visual alarms 208 through sensor interface 206, while auxiliary relay control output 262 allows a remote alarm output to be provided. In addition, the controller includes an RS-422 or equivalent interface 264 which allows interconnection with a telephone line. The controller is configured as known in the art, using appropriate programs stored in read-only memory 266 and/or programmable readonly memory 268.

In addition to display of the ORP and setpoint readings, the controller calculates the 0-1 volt output at control output 270 provided to inverter 218. Ozone output is inversely proportional to ORP, as contaminants lower the ORP to below the desired level.

Typically the ORP of water is in the range of 0-1000 mV, and it has been determined that an ORP of 650 mV resulting from ozonation provides an optimal level of organic oxidation. Thus, a setpoint in the range of 650 mV is chosen.

Alarm override switch 210 provides the alarm disable signal to prevent an alarm upon start-up. An appropriate status indicator 258 will indicate the override mode, as well as the alarm condition overridden. Setpoint switch 272 activates the watchdog system to guard against sustained constant ORP probe readings which might indicate probe problems. The system can be activated or disabled as desired. The electrodes are designed to operate at a transformer 240 primary current of 7.5 amps, which yields an ozone output of 30 grams/hr. By providing multiple electrodes, sufficient ozone production may be reached for any size cooling tower.

The controller is provided with operating power through 120v supply system 274, which is connected to line $L_1$ (FIG. 4) before the safety system such that it remains powered in the event of a system shutdown. This allows an appropriate alarm signal to be generated as required. While the sensor switches 180, 182, 188 and 196 are not connected directly to the controller, the operation of any of these switches, which leads to system shutdown, will have a prompt effect on the ORP sensed by the probe 200. This will result in an out-of-range condition being sensed by the controller, which will then activate the appropriate alarm outputs.

We claim:

1. An apparatus for controlling the condition of cooling tower system water, comprising
one or more ozone generator electrodes having inner and outer concentric electrode tubes, a concentric dielectric tube therebetween creating an annular space between said dielectric tube and outer electrode tube for the passage of oxygen-containing air for conversion of a portion of said oxygen to ozone and first and second opposed end caps for supporting said electrode tubes and dielectric tube in a concentric orientation and for the entry of air into and exit of ozone-containing air from said annular space;
means for providing dry, filtered input air at a depressed dewpoint and at constant flowrate to the first end caps of said electrodes;
sensor means for determining the oxidation-reduction potential of a water sample obtained from the system;
means coupled to said sensor means and to said ozone generator electrodes for maintaining the oxidation-reduction potential of said cooling tower system water at a target level in the range of about 550 to 6750 mv by comparing the determined oxidation-reduction potential with said target value and controlling the production of ozone in response thereto to allow the generation and maintenance of containment oxidation by-product secondary biocides at an elevated level;
means for combining the ozone produced by said electrodes with a portion of said cooling tower system water for return of resulting ozonated water to the system for introduction of the ozone thereto; and
means for monitoring the flow of said input air and the output of said electrodes whereby an alarm condition is indicated if said flow or output depart from established parameters.

2. The apparatus of claim 1, wherein said flow monitoring means comprise at least one pressure responsive sensor.

3. The apparatus of claim 2, whereby said monitoring means and said sensor means comprise a microprocessor.

4. The apparatus of claim 3, wherein said monitoring means includes means for overriding said alarm condition upon system start-up.

5. An apparatus for controlling the condition of cooling tower system water by variable ozonation to maintain the level of intermediate biocides at a desired elevated level, comprising
means for monitoring the oxidation-reduction potential of at least a portion of the cooling tower system water;
ozone-generating means for generating ozone and introducing said ozone generated into said water; and
control means coupled to said monitoring means and said ozone-generating means for maintaining the oxidation-reduction potential of said water at a target level in the range of about 550 to 650 my to promote the generation and maintenance of secondary biocides by adjusting the production of ozone by said ozone-generating means in a continuous manner in response to the oxidation-reduction potential sensed by said monitoring means.

6. The apparatus of claim 5, wherein said control means is adapted to maintain the oxidation-reduction potential in the range of 550 to 650 mV.

7. An apparatus for fostering the development and maintenance of secondary biocides in the water of a recirculating cooling water system, comprising
conduit means for removing a portion of the cooling water from the system for ozone treatment and returning the treated water to the system for blending with the contents thereof;
means for monitoring the oxidation-production potential of said removed portion prior to the ozone treatment thereof;
electrode means for generating ozone from the oxygen of ambient air passed through the electrode means, the output of said electrode means including said generated ozone;
control means coupled to said monitoring means and said electrode means for maintaining the oxidation-reduction potential of said cooling system water at a target level in the range of about 550 to 650 mv to maximize the generation and maintenance of intermediate biocide products of the oxidation of water contaminants by adjusting the production of ozone by said electrode means in response to the oxidation-reduction potential value sensed by said monitoring means; and
means for combining at least a portion of said removed portion of cooling system water with the ozone-containing output of said electrode means.

8. The apparatus of claim 7, wherein said electrode means are connected to a voltage source of approximately 860 hz.

9. The apparatus of claim 8, wherein the ozone production level of said electrodes is varied by adjusting the voltage applied to said electrodes.

10. The system of claim 9 including means for providing ambient air to said electrodes at a constant flow rate.

11. The apparatus of claim 7 further comprising means for passing said ambient air through said electrode means at a constant rate, and means for providing a varying voltage to said electrode means to control the ozone concentration of the output of said electrode means.

12. The apparatus of claim 11, wherein said control means is coupled to said electrode means by way of said means for providing a varying voltage.

13. The apparatus of claim 7, wherein said control means comprises means for adjusting the production of ozone as a function of the difference between the oxidation-reduction potential monitored by said monitoring means and said target level.

14. The apparatus of claim 13, wherein said control means further includes means to adjust the production of ozone in a continuous manner.

* * * * *

UNITED STATES PATENT AND TRADEMARK OFFICE
CERTIFICATE OF CORRECTION

PATENT NO.   : 5,236,673
DATED        : August 17, 1993
INVENTOR(S)  : TIMOTHY G. COAKLEY, et al.

It is certified that error appears in the above-identified patent and that said Letters Patent is hereby corrected as shown below:

Column 11, line 25 "6750 mv" should read
--650 mv--.

Signed and Sealed this

Fifteenth Day of March, 1994

Attest:

BRUCE LEHMAN

*Attesting Officer*          *Commissioner of Patents and Trademarks*